United States Patent [19]
Lindberg et al.

[11] Patent Number: 5,877,192
[45] Date of Patent: *Mar. 2, 1999

[54] METHOD FOR THE TREATMENT OF GASTRIC ACID-RELATED DISEASES AND PRODUCTION OF MEDICATION USING (-) ENANTIOMER OF OMEPRAZOLE

[75] Inventors: Per Lindberg, Mölndal; Lars Weidolf, Västra Frölunda, both of Sweden

[73] Assignee: Astra Aktiebolag, Sodertalje, Sweden

[*] Notice: The term of this patent shall not extend beyond the expiration date of Pat. No. 5,714,504.

[21] Appl. No.: 833,962

[22] Filed: Apr. 11, 1997

Related U.S. Application Data

[63] Continuation-in-part of Ser. No. 376,512, Jan. 23, 1995, Pat. No. 5,714,504, which is a continuation-in-part of Ser. No. 256,174, Jun. 28, 1994, Pat. No. 5,693,818.

[30] Foreign Application Priority Data

May 28, 1993 [SE] Sweden .................................. 9301830
Apr. 11, 1996 [SE] Sweden .................................. 9601383

[51] Int. Cl.$^6$ .................................................... A61K 31/44
[52] U.S. Cl. ............................ 514/338; 514/819; 514/927
[58] Field of Search ..................................... 514/338, 819, 514/927

[56] References Cited

U.S. PATENT DOCUMENTS 5,714,504  2/1998  Linberg et al. ......................... 514/338

*Primary Examiner*—Kimberly Jordan
*Attorney, Agent, or Firm*—White & Case LLP

[57] ABSTRACT

A method for treatment of gastric acid related diseases by inhibition of gastric acid secretion comprising administering to a mammal in need of treatment a therapeutically effective amount of the (−)-enantiomer of 5-methoxy-2-[[(4-methoxy-3,5-dimethyl-2-pyridinyl)methyl]sulfinyl]-1H-benzimidazole or a pharmaceutically acceptable salt thereof, so as to effect decreased interindividual variation in plasma levels upon administration. The use of the (−)-enantiomer of omeprazole to receive increased average plasma levels (AUC) upon administration of the same doses of the (−)-enantiomer of omeprazole compared to those of racemic omeprazole is also claimed, as well as an improved anti-secretory effect and a better clinical effect.

23 Claims, 3 Drawing Sheets

METHOD FOR THE TREATMENT OF GASTRIC ACID-RELATED DISEASES AND PRODUCTION OF MEDICATION USING (-) ENANTIOMER OF OMEPRAZOLE

This application is a continuation-in-part of Ser. No. 08/376,512 filed on Jan. 23, 1995 now U.S. Pat. No. 5,714,504, which is a continuation-in-part of Ser. No. 08/256,174 filed Jun. 28, 1994, now U.S. Pat. No. 5,693,818.

The description of the salt forms of the single enantiomers of omeprazole and the process of making the same is herein incorporated by reference to copending Ser. No. 08/376,512.

FIELD OF THE INVENTION

The present invention is related to the use of one of the single enantiomers of omeprazole, i.e. the (−)-enantiomer of 5-methoxy-2-[[(4-methoxy-3,5-dimethyl-2-pyridinyl)-methyl]sulfinyl]-1H-benzimidazole or a pharmaceutically acceptable salt thereof, in the treatment of gastric acid related diseases. The expression single enantiomer refers to the fact that the (−)-enantiomer is substantially free from its (+)-enantiomeric contaminant.

BACKGROUND OF THE INVENTION

The compound 5-methoxy-2-[[(4-methoxy-3,5-dimethyl-2-pyridinyl)methyl]sulfinyl]-1H-benzimidazole, having the generic name omeprazole, and therapeutically acceptable salts thereof, are described in EP 5129. The specific alkaline salts of omeprazole are described in EP 124 495. Omeprazole is effective as a gastric acid secretion inhibitor, and is useful as an antiulcer agent. In a more general sense, omeprazole may be used for prevention and treatment of gastric-acid related diseases in mammals and especially in man, including e.g. reflux esophagitis, gastritis, duodenitis, gastric ulcer and duodenal ulcer. Furthermore, omeprazole may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease (GERD), and in patients with gastrinomas. Omeprazole may also be used in patients in intensive care situations, in patients with acute upper gastrointestinal bleeding, pre-and postoperatively to prevent aspiration of gastric acid and to prevent and treat stress ulceration. Further, omeprazole may be useful in the treatment of psoriasis as well as in the treatment of Helicobacter infections and diseases related to these.

Omeprazole is a sulfoxide and a chiral compound, wherein the sulfur atom being the stereogenic center. Thus, omeprazole is a racemic mixture of its two single enantiomers, the (+)-enantiomer of omeprazole and the (−)-enantiomer of omeprazole. The absolute configurations of the enantiomers of omeprazole have been determined by an X-ray study of an N-alkylated derivative of the (+)-enantiomer in neutral form. The (+)-enantiomer of the neutral form and the (−)-enantiomer of the neutral form were found to have the R and S configuration, respectively. The conditions for the optical rotation measurement for each of the compounds mentioned above are described in WO 94/27988.

Different salts of the single enantiomers of omeprazole are also described in WO 94/27988. Specific processes for the preparation of the single enantiomers of substituted benzimidazoles are described in WO 96/02535. An oral pharmaceutical dosage form of omeprazole or one of its single enantiomers is described in WO 96/01623. Other oral dosage forms for the (−)-enantiomer of omeprazole can be found in EP 247 983.

There are few studies on the single enantiomers of omeprazole. One previous in vitro study on inhibition of acid secretion in isolated gastric glands showed no significant difference in effect between the two single enantiomers of omeprazole and the racemic mixture, see Erlandsson P. et al, Journal of Chromatography 1990; 532: 305–319. It has also been shown that, when omeprazole was administered intravenously to one subject, the plasma levels of the two enantiomers were similar, see Cairns A. M. et al, Journal of Chromatography B, 1995; 666: 323–328.

More than 135 million prescriptions by doctors indicate that omeprazole is an effective and safe drug. Notwithstanding, omeprazole exhibits polymorphic metabolism, i.e. a few individuals (3% among the Caucasian populations and 15–20% among Orientals) metabolise omeprazole slowly (slow metabolisers) compared to the rest of the population (rapid metabolisers). Slow metabolisers of omeprazole will obtain higher than the average plasma concentrations of the drug. Since the inhibition of gastric acid secretion is correlated to the area under the plasma concentration versus time curve (AUC), a more pronounced effect from omeprazole is expected in these slow metabolising individuals. A less interindividual variation, i.e. especially slow versus rapid metabolisers, and on the average higher plasma levels, giving higher dose efficiency in patients, could be of therapeutic benefit. Thus, one of the enantiomers of omeprazole, referred to as the (−)-enantiomer of omeprazole, or a pharmaceutically acceptable salt thereof, is hereby claimed to be an improved alternative to omeprazole in the treatment of gastric acid related diseases resulting in higher dose efficiency and in less interindividual variation in plasma levels (AUC), both between rapid and slow metabolisers and within the group of rapid metabolisers.

SUMMARY OF THE INVENTION

The use of the (−)-enantiomer of omeprazole, or a pharmaceutically acceptable salt thereof, in the treatment of gastric acid related diseases as a mean to decrease interindividual variation in plasma levels compared to omeprazole is claimed. The use of the (−)-enantiomer of omeprazole to receive increased average plasma levels (AUC) of the substance compared to those of racemic omeprazole and thereby a higher dose efficiency is also claimed.

DETAILED DESCRIPTION OF THE DRAWINGS

DETAILED DESCRIPTION OF THE INVENTION

Figure 1:
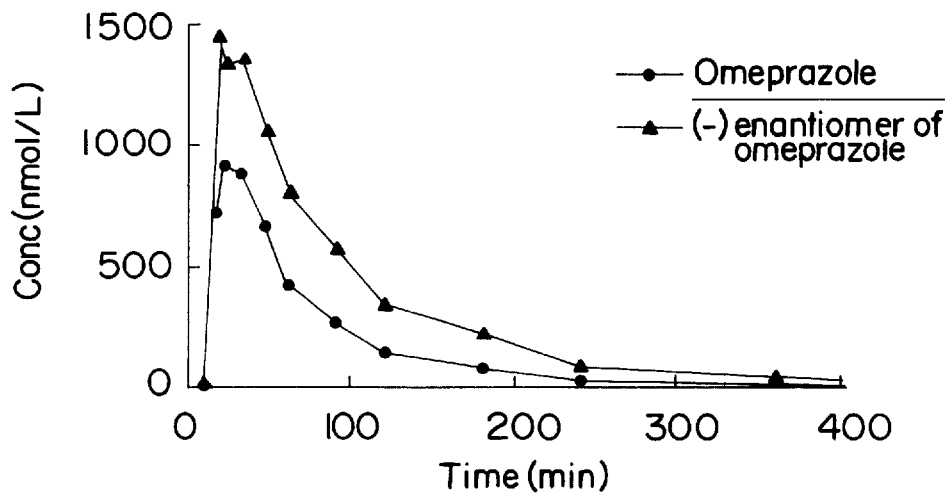
FIG. 1 shows the mean plasma levels of racemic omeprazole and the (−)-enantiomer of omeprazole at steady state (Day 7) in rapid metabolisers following administration of 15 mg doses of each substance.

Omeprazole is metabolised mainly in the liver by the cytochrome P450 system (CYP). Metabolism can be defined as the property of the body to transform lipophilic compounds into hydrophilic derivatives, which more easily can be excreted from the body. The metabolism can generally be divided into phase I and phase II reactions. During a phase I reaction, polar groups are formed via oxidation, hydroxylation, or hydrolysis. These reactions are mainly associated with the CYP enzymes. Phase II reactions are conjugation reactions, in which even further hydrophilic moities are attached to the drug or to its metabolites.

CYP is a superfamily of enzymes. Each family consists of one or more subfamilies and each subfamily contains one or more specific CYP isoforms. Apart from metabolising drugs, the CYP isoforms also have the property to metabolise endogenous compounds, such as steroids, fatty acids, and prostaglandins.

With respect to drug metabolism in man, three families, CYP1, CYP2, and CYP3 or, more specifically, six different CYP isoforms within these families are of particular importance. Each isoform demonstrates a certain substrate specificity. The expression of these enzymes is under genetic control, which is one of the reasons for the interindividual variation in rate and extent of metabolism demonstrated for most drugs. Moreover, at least two of the CYP isoforms, CYP2C19 and CYP2D6, are polymorphically expressed. Thus, a few individuals among the population, i.e. the slow metabolisers, lack or express a mutated form of the relevant CYP isoform, and consequently metabolise substrates for this isoform slowly. Metabolism still occurs in these slow metabolisers, although at a lower rate, because it is switched to other CYP isoforms which are less important for the metabolism of the substrate in the rest of the population.

Omeprazole is known to be a substrate for the polymorphically expressed CYP2C19. In vitro studies in human liver microsomes have surprisingly indicated that the (−)-enantiomer of omeprazole is less metabolised by CYP2C19 than omeprazole. In agreement with this, it has also been found, according to the present invention, that administration of the (−)-enantiomer of omeprazole or an acceptable therapeutical salt thereof results in a less pronounced difference in plasma levels between slow and rapid metabolisers.

Some studies have been published indicating that slow metabolisers, with higher than average plasma concentrations of omeprazole, are more prone to develop hypergastrinemia (Chang M. et al. Br J Clin Pharmacol 995; 39: 511–518, Caraco Y. et al. Clin Pharmacol Ther 1996; 59, 2: 216) as well as to slightly induce the levels of CYP1A2 (Rost KL et al. Clin Pharmacol Ther 1992; 52: 170–180, Rost KL et al. Clin Pharmacol Ther 1994; 55: 402–411), a CYP isoform distinct from CYP2C19. Some authors have therefore suggested that there might be a need for dosage adjustment in these individuals. The use of the (−)-enantiomer of omeprazole would decrease the potential for CYP1A2 induction in slow metabolisers as a result of the lower plasma levels (AUC) of this compound obtained in these individuals. Since the gastrin levels obtained simply are a result of a natural feedback mechanism determined by the degree of inhibition of gastric acid secretion, the use of the (−)-enantiomer of omeprazole may also potentially result in a less pronounced increase in gastrin in slow metabolisers.

The clinical study reported below supports the claimed invention and discusses the results more in detail.

The (−)-enantiomer of omeprazole is effective as a gastric acid secretion inhibitor, and is useful as an antiulcer agent. In a more general sense, the (−)-enantiomer of omeprazole can be used for prevention and treatment of the same gastric-acid related diseases in mammals and especially in man as omeprazole, see above.

Any suitable route of administration may be employed for providing the patient with an effective dosage of the (−)-enantiomer of omeprazole. For example, oral, parenteral, subcutaneous, intramuscular, rectal, transdermal and the like may be employed. Dosage forms include capsules, tablets, dispersions, suspensions, solutions and the like.

The pharmaceutical compositions of the present invention comprise the (−)-enantiomer of omeprazole as active ingredient, or a pharmaceutically acceptable salt thereof, and may also contain a pharmaceutically acceptable carrier and optionally other therapeutic ingredients. The term "pharmaceutically acceptable salt" refers to both acid and alkaline pharmaceutically acceptable non-toxic salts. Compositions comprising other therapeutic ingredients are especially of interest in the treatment of Helicobacter infections.

The compositions include compositions suitable for oral, rectal or parenteral such as subcutaneous, intramuscular, and intravenous administration. The most preferred route of the present invention is the oral route. The compositions may be conveniently presented in unit dosage forms, and prepared by any methods well known in the art of pharmacy.

The most suitable route of administration as well as the magnitude of a therapeutic dose of the (−)-enantiomer of omeprazole or a pharmaceutically acceptable salt thereof in any given case will depend on the nature and severity of the disease to be treated. The dose, and dose frequency, may also vary according to the age, body weight, and response of the individual patient. Special requirements may be needed for patients having Zollinger-Ellison syndrome, such as a need for higher doses than the average patient. Children and patients with liver diseases generally will benefit from doses that are somewhat lower than the average. Thus, in some conditions it may be necessary to use doses outside the ranges stated below. Such higher and lower doses of the (−)-enantiomer of omeprazole are within the scope of the present invention.

In general, a suitable oral dosage form may cover a dose range from 5 mg to 80 mg total daily dose, administered in one single dose or equally divided doses. A preferred dose range is from 20 mg to 60 mg total daily dose. For a parenteral dosage form the same dose ranges may apply.

The (−)-enantiomer of omeprazole may be combined as the active component in intimate admixture with a pharmaceutical carrier according to conventional techniques, such as the oral formulations described in WO 96/ 01623 and EP 247 983, the disclosures of which are hereby incorporated in a whole by reference.

Different routes of preparation of the (−)-enantiomer of omeprazole and pharmaceutically acceptable salts thereof are described in WO 94/ 27988 and WO 96/ 02535, the disclosures of which are hereby incorporated in a whole by reference.

The invention is further defined by reference to the following experimental work describing in detail the study and results as well as the clinical relevance of the findings.

EXPERIMENTAL STUDY

Methods:

In an open, randomised, three way cross-over designed study, consisting of three treatment periods, each with a duration of 7 days and each separated by a washout period of two weeks, the sodium salt of the (−)-enantiomer of omeprazole, the sodium salt of the (+)-enantiomer of omeprazole and omeprazole sodium salt were investigated. Nine healthy subjects, classified according to the urinary S/R mephenytoin ratio as five slow metabolisers and four rapid metabolisers of omeprazole, completed the study (Sanz E. J. et al, Clin Pharmacol Ther 1989; 45:495–499).

In slow metabolisers 60 mg doses of each compound were given once daily, while the rapid metabolisers were given once daily doses of 15 mg. The pharmacokinetics were studied in all subjects on days 1 and 7. The reason for using different doses was to optimise the conditions to explore the secondary aims of the study, to measure the effect on gastric acid secretion in rapid metabolisers and to measure the potential effect on caffeine metabolism in slow metabolisers.

Results and discussion:

In rapid metabolisers the mean AUC at steady state (Day 7) of the (−)-enantiomer of omeprazole was almost 90% higher than that of omeprazole. (FIG. 1). This resulted in a more pronounced gastric acid antisecretory effect for the (−)-enantiomer of omeprazole compared to that of omeprazole. The inhibition of pentagastrin stimulated gastric acid secretion was 62% for omeprazole and 79% for the (−)-enantiomer of omeprazole following administration of 15 mg doses of each substance.

Figure 2:
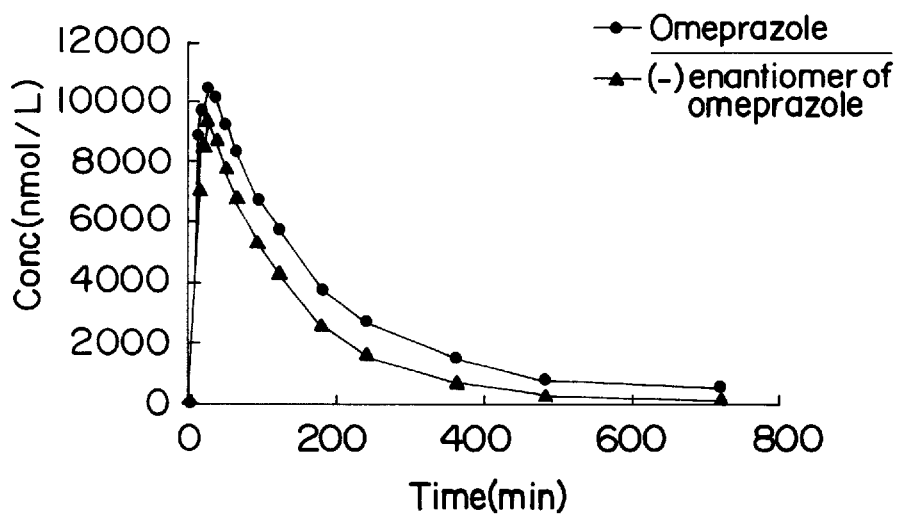
FIG. 2 shows the mean plasma levels of racemic omeprazole and the (−)-enantiomer of omeprazole at steady state (Day 7) in slow metabolisers following administration of 60 mg doses of each substance.
Figure 3A:
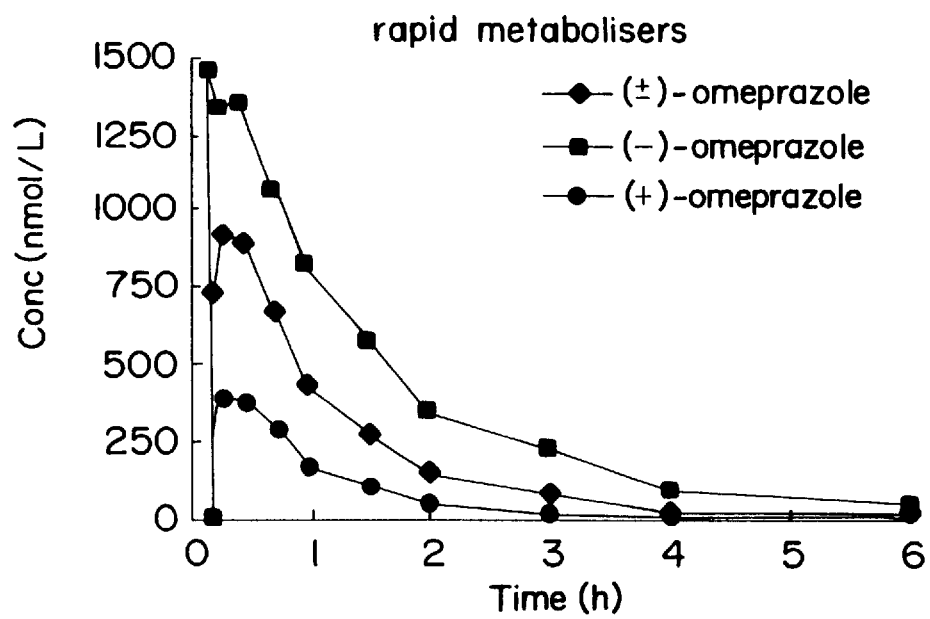
FIGS. 3a and 3b show the mean plasma levels of racemic omeprazole, the single (−)-enantiomer of omeprazole and the single (+)-enantiomer of omeprazole at steady state in rapid and slow metabolisers following administration of 15 mg and 60 mg doses of each substance, respectively. The figure sheet also comprises the ratios between the mean AUCs at steady state of slow and rapid metabolisers.
Figure 3B:
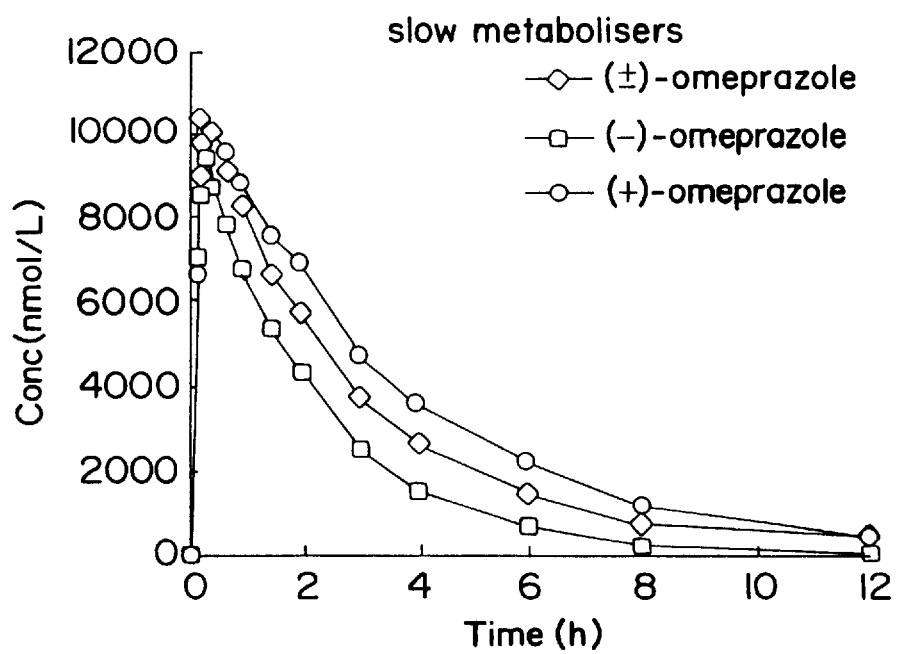

In slow metabolisers the mean AUC at steady state (Day 7) of the (−)-enantiomer of omeprazole was about 30% lower than that of omeprazole. (FIG. 2). Thus, after correction for different dose levels, the resulting difference in AUC between slow and rapid metabolisers was almost 10-fold for omeprazole and only 3-fold for the (−)-enantiomer of omeprazole. With the (+)-enantiomer of omeprazole, on the other hand, the difference in AUC was much greater, approximately 30-fold (FIG. 3).

In conclusion, the interindividual variation in plasma levels upon administration of the (−)-enantiomer of omeprazole will be less than for omeprazole and more patients will get optimal plasma concentrations with respect to gastric acid antisecretory effect and potentially also a better clinical effect following administration of the same doses.

Another study was conducted in 38 patients with symptomatic gastroesophageal reflux disease in which the effects on 24 hour intragastric acidity by oral treatment with 20 mg omeprazole racemate (capsules) and the magnesium salt of (−)-omeprazole (corresponding to 20 mg or 40 mg of the neutral compound) were compared. In addition, the plasma concentrations of (−)-omeprazole and omeprazole racemate were determined on the last treatment day (day 5).

The study was conducted as a double-blind, randomized, three-way cross-over trial consisting of three study periods, each with five days of daily oral administration of formulations containing the magnesium salt of (−)-omeprazole or omeprazole racemate separated by a wash-out period of at least two weeks. The 38 patients (22 females) ranged in age from 29–58 years. 32 of the patients were *Helicobacter pylori* negative.

Enteric coated pellets comprising the magnesium salt of (−)-omeprazole were filled in hard gelatin capsules calculated to correspond to either 20 mg or 40 mg of neutral (−)-omeprazole compound.

These formulations were compared with an identical treatment except for using enteric coated pellets comprising omeprazole filled in a hard gelatin capsule containing 20 mg racemic omeprazole in the non-salt form (Prilosec®).

The intragastric pH was recorded over 24 hours on day five of each study period upon administering the fifth dose. The study was completed by 36 patients and the results therefrom were statistically evaluated. The effects of the treatments on intragastric pH are summarized in Table 1 and the AUC values are shown in Table 2.

As shown in Table 1 the percentage of time (of the 24-hour period assessed) with pH above 4 (a direct measure of inhibitory effect on gastric acid secretion) was 44% for 20 mg omeprazole racemate and 53% for 20 mg (−)-omeprazole (p<0.0001), which means that patients treated with (−)-omeprazole will have 2.2 hours longer time with pH above 4 than those treated with omeprazole racemate in corresponding doses.

TABLE 1

Least square estimates and 95% confidence intervals for the true mean treatment effects, regarding percentage of time with pH > 4 during 24 hours.

| Treatment | | Estimate | Lower | Upper |
|---|---|---|---|---|
| Omeprazole | 20 mg | 43.7 | 36.7 | 50.7 |
| (−)ome | 20 mg | 53.0 | 46.0 | 60.0 |
| (−)ome | 40 mg | 69.8 | 62.8 | 76.8 |

The data of Table 2 shown below demonstrate that the AUC of (−)omeprazole is significantly higher than that of racemic omeprazole at the 20 mg dose, and the 40 mg dose of (−)omeprazole produced a significantly higher AUC than the 20 mg dose of (−)-omeprazole (p<0.0001).

The interindividual variation in AUC and thus the inhibitory effect is less pronounced following administration of (−)-omeprazole than following administration of omeprazole racemate. This was judged by the coefficient of variation for the mean AUC which was 59% for 20 mg of the magnesium salt of (−)-omeprazole and 88% for 20 mg of omeprazole racemate (p<0.0001).

TABLE 2

Least square estimates and 95% confidence intervals for the true mean treatment effects, regarding AUC (μmol × h/L).

| Treatment | | Estimate | Lower | Upper |
|---|---|---|---|---|
| Omeprazole | 20 mg | 2.3 | 1.8 | 3.0 |
| (−)ome | 20 mg | 4.2 | 3.3 | 5.4 |
| (−)ome | 40 mg | 12.6 | 9.9 | 16.2 |

As a consequence of the less pronounced difference in AUC between slow and rapid metabolizers, the interindividual variation in AUC of (−)-omeprazole is less than that of omeprazole. Furthermore, available data indicate that the interindividual variation in AUC of (−)omeprazole within the group of rapid metabolizers also is less than that observed for omeprazole racemate. These characteristics taken together may potentially result in a larger fraction of patients attaining plasma concentrations which would be optimal with respect to the desired gastric acid anti-secretory effect in the clinical situation.

It was observed that the steady-state AUC of (−)-omeprazole in an average population was significantly higher (2-fold) than that of omeprazole racemate when each compound was given repeatedly in 20 mg daily doses. Therefore, the anti-secretory effect, which is directly correlated to the AUC irrespective of compound, was higher for (−)-omeprazole than for omeprazole racemate following administration of identical doses. This is expected to give a clinical advantage for (−)-omeprazole, since the number of patients healed from the acid-related disease is expected to be higher, and healing is also expected to be achieved within a shorter time frame. It might also be expected that a more rapid symptom relief will be obtained.

The clinical studies outlined above demonstrate that the alkali metal salts of (−)-omeprazole have unexpected pharmacokinetic advantages over the omeprazole racemate, such as less interindividual variation in plasma levels (AUC) both between rapid and slow metabolizers and within the group of rapid metabolizers. The alkali metal salts of (−)-omeprazole provide for a larger fraction of patients with optimal plasma concentrations with respect to desired antisecretory effect. Higher average AUC results in a more pronounced inhibitory effect on gastric-acid secretion and is expected to result in a better overall clinical effect. Thus, the alkaline salts of (−)-omeprazole can provide an improved, alternative pharmaceutical formulation and method for the treatment of gastric acid-related diseases.

What is claimed is:

1. A method for treatment of gastric acid related diseases by inhibition of gastric acid secretion comprising administering to a mammal in need of treatment a therapeutically effective amount of a proton pump inhibitor consisting essentially of the (−)-enantiomer of 5-methoxy-2-[[(4-methoxy-3,5-dimethyl-2-pyridinyl)methyl]sulfinyl]-1H-benzimidazole or a pharmaceutically acceptable salt thereof, so as to effect decreased interindividual variation in plasma levels (AUC) during treatment of gastric acid related diseases.

2. A method for treatment of gastric acid related diseases by inhibition of gastric acid secretion comprising administering to a mammal in need of treatment a therapeutically effective amount of a proton pump inhibitor consisting essentially of the (−)-enantiomer of 5-methoxy-2-[[(4-methoxy-3,5-dimethyl-2-pyridinyl)methyl]sulfinyl]-1H-benzimidazole or a pharmaceutically acceptable salt thereof, so as to effect an increased average plasma levels (AUC) per dosage unit.

3. The method according to claim 1 or 2 so as to effect a less pronounced increase in gastrin levels in slow metabolisers during treatment of gastric acid related diseases.

4. The method according to claim 1 or 2 so as to effect a decreased CYP1A induction in slow metabolisers during treatment of gastric acid related diseases.

5. The method according to claim 1 or 2 so as to elicit an improved antisecretory effect during the treatment of gastric acid related diseases.

6. The method according to claim 1 or 2 so as to elicit an improved clinical effect comprising accelerated rate of healing and accelerated rate of symptom relief during the treatment of gastric related diseases.

7. The method according to claim 1 or 2, wherein the (−)-enantiomer of omeprazole or a pharmaceutically acceptable salt thereof, is administered orally in the form of a tablet or a capsule.

8. The method according to claim 1 or 2, wherein the (−)-enantiomer of omeprazole or a pharmaceutically acceptable salt thereof, is administered parenterally.

9. The method according to claim 1 or 2, wherein the (−)-enantiomer of omeprazole or a pharmaceutically acceptable salt thereof, is administered by intravenous infusion.

10. The method according to claim 1 or 2, wherein the amount administered is about 5–80 mg total daily dose.

11. The method according to claim 1 or 2, wherein the amount administered is about 20–60 mg total daily dose.

12. A method for the production of a medicament for treating gastric acid related diseases, which comprises: combining a therapeutically effective amount of a proton pump inhibitor consisting essentially of the (−)-enantiomer of 5-methoxy-2-[[(4-methoxy-3,5dimethyl-2-pyridinyl)methyl]sulfinyl]-1H-benzimidazole or a pharmaceutically acceptable salt thereof, with a pharmaceutically acceptable carrier.

13. The method according to claim 12, wherein the medicament causes a decreased interindividual variation in plasma levels (AUC) per unit dosage during the treatment of gastric acid related diseases.

14. The method according to claim 12, wherein the medicament causes an increased average plasma level (AUC) per unit dosage during the treatment of gastric acid related diseases.

15. The method according to claim 12, wherein the medicament causes a less pronounced increase in gastrin levels in slow metabolisers during treatment of gastric acid related diseases.

16. The method according to claim 12, wherein the medicament causes a decreased CYP1A induction in slow metabolisers during treatment of gastric acid related diseases.

17. The method according to claim 12, wherein the medicament causes an improved antisecretory effect during the treatment of gastric acid related diseases.

18. The method according to claim 12, wherein the medicament causes an improved clinical effect comprising accelerated rate of healing and accelerated rate of symptom relief during the treatment of gastric related diseases.

19. The method according to claim 12, wherein the medicament produced for oral administration is in the form of a tablet or capsule.

20. The method according to claim 12, wherein the medicament is administered parentally, by intravenous infusion.

21. The method according to any of claims 12–20, wherein the medicament is administered in the amount of about 5 mg to 80 mg total daily dose.

22. The method according to any of claims 12–20, wherein the medicament is administered in the amount of about 20 mg to 60 mg total daily dose.

23. The method according to claim 1 or 2 wherein the (−)-enantiomer of the proton pump inhibitor is essentially devoid of its (+)-enantiomeric contaminant.

* * * * *

UNITED STATES PATENT AND TRADEMARK OFFICE
CERTIFICATE OF CORRRECTION

PATENT NO. : 5,877,192  
DATED : March 2, 1999  
INVENTOR(S) : Per Lindberg, et al.

Page 1 of 4

It is certified that error appears in the above-identified patent and that said Letters Patent is hereby corrected as shown below:

On the title page insert the following under item [56]:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 6 | 3 | 6 | 4 | 9 | 9 | 1/13/96 | Brandstrom et al | | | |
| | | 5 | 0 | 4 | 5 | 3 | 2 | 1 | 9/3/91 | Makino et al | | | |
| | | 4 | 7 | 3 | 8 | 9 | 7 | 4 | 4/19/88 | Brandstrom et al | | | |
| | | 4 | 8 | 5 | 3 | 2 | 3 | 0 | 8/1/89 | Lovgren et al | | | |
| | | 4 | 7 | 8 | 6 | 5 | 0 | 5 | 11/22/88 | Lovgren et al | | | |

FOREIGN PATENT DOCUMENTS

| | | DOCUMENT NUMBER | | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|---|
| | | 4 | 0 | 3 | 5 | 4 | 5 | 5 | 11/90 | DE | | | | |
| | | 0 | 1 | 2 | 4 | 4 | 9 | 5 | 1/14/87 | EP | | | | |

UNITED STATES PATENT AND TRADEMARK OFFICE
CERTIFICATE OF CORRRECTION

PATENT NO. : 5,877,192  
DATED : March 2, 1999  
INVENTOR(S) : Per Lindberg, et al.

Page 2 of 4

It is certified that error appears in the above-identified patent and that said Letters Patent is hereby corrected as shown below:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 6 | 0 | 1 | 6 | 2 | 3 | 1/25/96 | WIPO | | | |
| | | 0 | 0 | 0 | 5 | 1 | 2 | 9 | 4/29/81 | EP | | | |
| | | 0 | 3 | 6 | 5 | 9 | 4 | 7 | 5/2/90 | EP | | | |
| | | 9 | 5 | 0 | 1 | 7 | 8 | 3 | 1/19/95 | WIPO | | | |
| | | 9 | 2 | 2 | 2 | 2 | 8 | 4 | 12/23/92 | WIPO | | | |
| | | 9 | 6 | 0 | 2 | 5 | 3 | 5 | 2/1/96 | WIPO | | | |
| | | 9 | 4 | 2 | 7 | 9 | 8 | 8 | 12/8/94 | WIPO | | | |
| | | 6 | 2 | 4 | 7 | 9 | 8 | 3 | 4/16/87 | EP | | | |

UNITED STATES PATENT AND TRADEMARK OFFICE
CERTIFICATE OF CORRRECTION

PATENT NO. : 5,877,192
DATED : March 2, 1999
INVENTOR(S) : Per Lindberg, et al.

Page 3 of 4

It is certified that error appears in the above-identified patent and that said Letters Patent is hereby corrected as shown below:

OTHER DOCUMENTS

|   |   |   |
|---|---|---|
|   | Cairns, et al. "Enantioselective HPLC determination..." Journal of Chromatography | |
|   | 8,666 (1995) 323-328 | |
|   | Yamada et al. "Synthesis and isomerization of optical active.." Chem. Pharm. Bull. | |
|   | 42(8) (1994) 1679-1681 | |
|   | K. Miwa et al. "Jpn. Pharmacol. Ther. "Proton pump inhibitor in rats, mice and dogs" | |
|   | 18 (1990) 165-187 (transl.) | |
|   | H. Katsuki et al. "Determination of R(+)- and S(-)-Lansoprazole" Pharmaceutical | |
|   | Research 13(4) (1996) 611-615 | |
|   | M. Tanaka et al. "Direct determination of pantoprazole enantiomers..." Anal. Chem. | |
|   | 68 (1996) 1513-1516 | |
|   | Erlandson et al. "Resolution of the enantiomers of omeprazole..." J. Chromatography | |
|   | (1990) 532: 305-319 | |
|   | Chang et al. 1995 "Interphenotype differences..." Brit. J. Clinical Pharmacology 39: 511-518 | |

UNITED STATES PATENT AND TRADEMARK OFFICE
CERTIFICATE OF CORRRECTION

PATENT NO. : 5,877,192
DATED : March 2, 1999
INVENTOR(S) : Per Lindberg, et al.

It is certified that error appears in the above-identified patent and that said Letters Patent is hereby corrected as shown below:

OTHER DOCUMENTS

|   |   |
|---|---|
|   | A. Brandstrom "Chemical reactions..." Reprint from ACTA CHEMICA SCANDINAVICA" |
|   | 43 (1989) 536-611 |
|   | K. Sigrist-Nelson et al. "Ro 18-5364, a potent inhibitor of the gastric (H + K) -ATPase" |
|   | Eur. J. Bioch. 166 (1987) 453 |
|   | Palomo Coll, Alberto (1992) "Preparation of alkali metal salts of omeprazole..." CA |
|   | No. 117: 90292 |
|   | Rost et al. (1994) "Accelerated caffeine metabolism after omeprazole..." |
|   | 55: 402-411 |
|   | Rost et al. (1992) " Increase of cytochrane P450IA2 activity..." |
|   | 52: 170-180 |
|   | Marle et al. "Determination of binding affinity of enantiomers..." J. Chromatography |
|   | (1988) 456: 323-336 |

Signed and Sealed this

Twenty-seventh Day of April, 1999

*Attest:*

Q. TODD DICKINSON

*Attesting Officer*     *Acting Commissioner of Patents and Trademarks*